(12) United States Patent
Lee et al.

(10) Patent No.: US 12,217,335 B2
(45) Date of Patent: Feb. 4, 2025

(54) METHOD AND APPARATUS FOR ACQUIRING CBCT IMAGE BASED ON ADAPTIVE SAMPLING

(71) Applicant: UIF (University Industry Foundation), Yonsei University, Seoul (KR)

(72) Inventors: Ho Lee, Seoul (KR); Ik Jae Lee, Seoul (KR)

(73) Assignee: UIF (University Industry Foundation), Yonsei University, Seoul (KR)

( * ) Notice: Subject to any disclaimer, the term of this patent is extended or adjusted under 35 U.S.C. 154(b) by 331 days.

(21) Appl. No.: 17/812,289

(22) Filed: Jul. 13, 2022

(65) Prior Publication Data

US 2023/0030889 A1  Feb. 2, 2023

(30) Foreign Application Priority Data

Jul. 20, 2021  (KR) .................. 10-2021-0094913

(51) Int. Cl.
  *G06T 11/00* (2006.01)
  *A61B 6/03* (2006.01)

(52) U.S. Cl.
  CPC ........... *G06T 11/005* (2013.01); *A61B 6/032* (2013.01); *G06T 11/006* (2013.01); *G06T 2210/41* (2013.01); *G06T 2211/424* (2013.01)

(58) Field of Classification Search
  CPC . G06T 11/005; G06T 11/006; G06T 2210/41; G06T 2211/424; A61B 6/032; A61B 6/54; A61B 6/545; A61B 6/547; A61B 6/4085; A61B 6/5211; A61B 6/5223
  See application file for complete search history.

(56) References Cited

U.S. PATENT DOCUMENTS

| | | | | |
|---|---|---|---|---|
| 11,232,543 | B2* | 1/2022 | Wang | G06T 7/11 |
| 2020/0066006 | A1* | 2/2020 | Dwivedi | G16H 30/40 |
| 2020/0240934 | A1* | 7/2020 | Yi | G06T 5/20 |
| 2020/0334870 | A1* | 10/2020 | Bai | G06T 11/006 |
| 2021/0390668 | A1* | 12/2021 | Ren | G06T 5/70 |
| 2023/0162412 | A1* | 5/2023 | Cachovan | G06T 11/008 345/419 |

FOREIGN PATENT DOCUMENTS

| | | | |
|---|---|---|---|
| KR | 10-2015-0016054 A | | 2/2015 |
| KR | 20150016054 A | * | 2/2015 |
| KR | 10-2015-0047109 A | | 5/2015 |
| KR | 10-2016-0140525 A | | 12/2016 |
| KR | 10-2017-0032818 A | | 3/2017 |
| WO | 01/33251 A1 | | 5/2001 |

OTHER PUBLICATIONS

Office Action for KR 10-2021-0094913 by Korean Intellectual Property Office dated Jan. 2, 2023.

* cited by examiner

*Primary Examiner* — Oneal R Mistry
*Assistant Examiner* — Jongbong Nah
(74) *Attorney, Agent, or Firm* — BROADVIEW IP LAW, PC

(57) ABSTRACT

According to the method and the apparatus for acquiring a CBCT image based on adaptive sampling according to the exemplary embodiment of the present disclosure, a final CBCT image is acquired by reconstructing a plurality of cone beam computed tomography (CBCT) images acquired based on adaptive sampling so that a dose applied to the target patient may be reduced.

11 Claims, 13 Drawing Sheets

100

METHOD AND APPARATUS FOR ACQUIRING CBCT IMAGE BASED ON ADAPTIVE SAMPLING

CROSS-REFERENCE TO RELATED APPLICATIONS

This application is based on and claims priority under 35 U.S.C. 119 to Korean Patent Application No. 10-2021-0094913 filed in the Korean Intellectual Property Office on Jul. 20, 2021, the entire contents of which are herein incorporated by reference in its entirety.

BACKGROUND

Field

The present disclosure relates to a method and an apparatus for acquiring a CBCT image based on adaptive sampling, and more particularly, to a method and an apparatus for acquiring a cone beam computed tomography (CBCT) image.

This work was supported by the National Research Foundation of Korea (NRF) grant funded by the Korea government (MSIT) (2022R1A2C2011556).

Description of the Related Art

FIG. 1 is a view for explaining an operating process of a CBCT imaging system of the related art and FIG. 2 is a view illustrating an example of the operating process illustrated in FIG. 1.

Referring to FIG. 1, a cone beam computed tomography imaging system 10 of the related art includes a rotating gantry, a couch on which a target patient is located, a radiation irradiator which is installed on the gantry to irradiate a radiation beam, and an image acquiring unit which is installed on the gantry to acquire an image by detecting a radiation beam which penetrates the target patient.

As illustrated in FIGS. 1 and 2, the CBCT imaging system of the related art acquires a plurality of CBCT images for the target patient while rotating the gantry at a constant sampling interval. That is, the CBCT imaging system 10 of the related art acquires a plurality of CBCT images by means of uniform sampling.

SUMMARY

An object to be achieved by the present disclosure is to provide a method and an apparatus for acquiring a CBCT image based on adaptive sampling which reconstructs a plurality of cone beam computed tomography (CBCT) images acquired based on adaptive sampling to acquire a final CBCT image.

Other and further objects of the present disclosure which are not specifically described can be further considered within the scope easily deduced from the following detailed description and the effect.

In order to achieve the above-described object, according to an aspect of the present disclosure, a CBCT image acquiring method based on adaptive sampling includes: a step of acquiring a plurality of image scanning points based on a previously acquired medical image for a target patient; a step of acquiring a plurality of cone beam computed tomography (CBCT) images for the target patient based on the plurality of image scanning points; and a step of acquiring a final CBCT image for the target patient based on the plurality of CBCT images.

Here, the step of acquiring a plurality of image scanning points is configured by acquiring an image for every image scanning point based on the medical image, sorting images for image scanning points based on a quantitative value for each of images for image scanning points, selecting a plurality of images according to a predetermined criterion, among sorted images for image scanning points, and acquiring the image scanning points corresponding to the plurality of selected images as the plurality of image scanning points.

Here, the step of acquiring a plurality of image scanning points is configured by sorting images for image scanning points based on an entropy for each of acquired images for image scanning points.

Here, the step of acquiring a plurality of image scanning points is configured by sorting the images for image scanning points in a descending order based on a quantitative value for each of the acquired images for image scanning points and selecting a plurality of images in the order of larger quantitative values, among the sorted images for image scanning points.

Here, the step of acquiring a plurality of image scanning points is configured by acquiring the image for every image scanning point from the medical image by means of forward projection, using geometric information of a CBCT imaging system.

Here, the step of acquiring a plurality of CBCT images is configured by scanning the target patient at the plurality of image scanning points by means of the CBCT scanning system to acquire the plurality of CBCT images.

Here, the step of acquiring a final CBCT image is configured by acquiring a final CBCT image based on the plurality of CBCT images using one of the analytical reconstruction algorithm and the iterative reconstruction algorithm.

Here, the medical image is a computed tomography volume image and the image scanning point is a gantry rotational index.

In order to achieve the above-described technical objects, according to an aspect of the present disclosure, a computer program is stored in a computer readable storage medium to allow a computer to execute any one of the above CBCT image acquiring methods based on adaptive sampling.

In order to achieve the above-described objects, according to an aspect of the present disclosure, a CBCT image acquiring apparatus based on adaptive sampling is a CBCT image acquiring apparatus which reconstructs a plurality of cone beam computed tomography images acquired based on adaptive sampling to acquire a final CBCT image and includes: a memory which stores one or more programs to acquire the final CBCT image by reconstructing the plurality of CBCT images acquired based on adaptive sampling; and one or more processors which performs an operation for reconstructing the plurality of CBCT images acquired based on adaptive sampling according to one or more programs stored in the memory to acquire the final CBCT image, the processor acquires a plurality of image scanning points based on a previously acquired medical image for a target patient, acquires the plurality of CBCT images for the target patient based on the plurality of image scanning points, and acquires a final CBCT image for the target patient based on the plurality of CBCT images.

Here, the processor acquires an image for every image scanning point based on the medical image, sorts images for image scanning points based on a quantitative value for each of images for image scanning points, selects a plurality of images according to a predetermined criterion, among sorted images for image scanning points, and acquires the image scanning points corresponding to the plurality of selected images as the plurality of image scanning points.

Here, the processor sorts images for image scanning points based on an entropy for each of acquired images for image scanning points.

Here, the processor sorts the images for image scanning points in a descending order based on a quantitative value for each of the acquired images of every image scanning point and selects a plurality of images in the order of larger quantitative values, among the sorted images for image scanning points.

According to the method and the apparatus for acquiring a CBCT image based on adaptive sampling according to the exemplary embodiment of the present disclosure, a final CBCT image is acquired by reconstructing a plurality of cone beam computed tomography (CBCT) images acquired based on adaptive sampling so that a dose applied to the target patient may be reduced.

The effects of the present invention are not limited to the technical effects mentioned above, and other effects which are not mentioned can be clearly understood by those skilled in the art from the following description

BRIEF DESCRIPTION OF THE DRAWINGS

FIGS. 4A and 4B are views for explaining an example of implementing the CBCT image acquiring apparatus illustrated in FIG. 3 in which FIG. 4A illustrates that the CBCT image acquiring apparatus and a CBCT imaging system are implemented as independent apparatuses and FIG. 4B illustrates that the CBCT image acquiring apparatus and the CBCT imaging system are integrally implemented;

DETAILED DESCRIPTION OF THE EMBODIMENT

Figure 1:
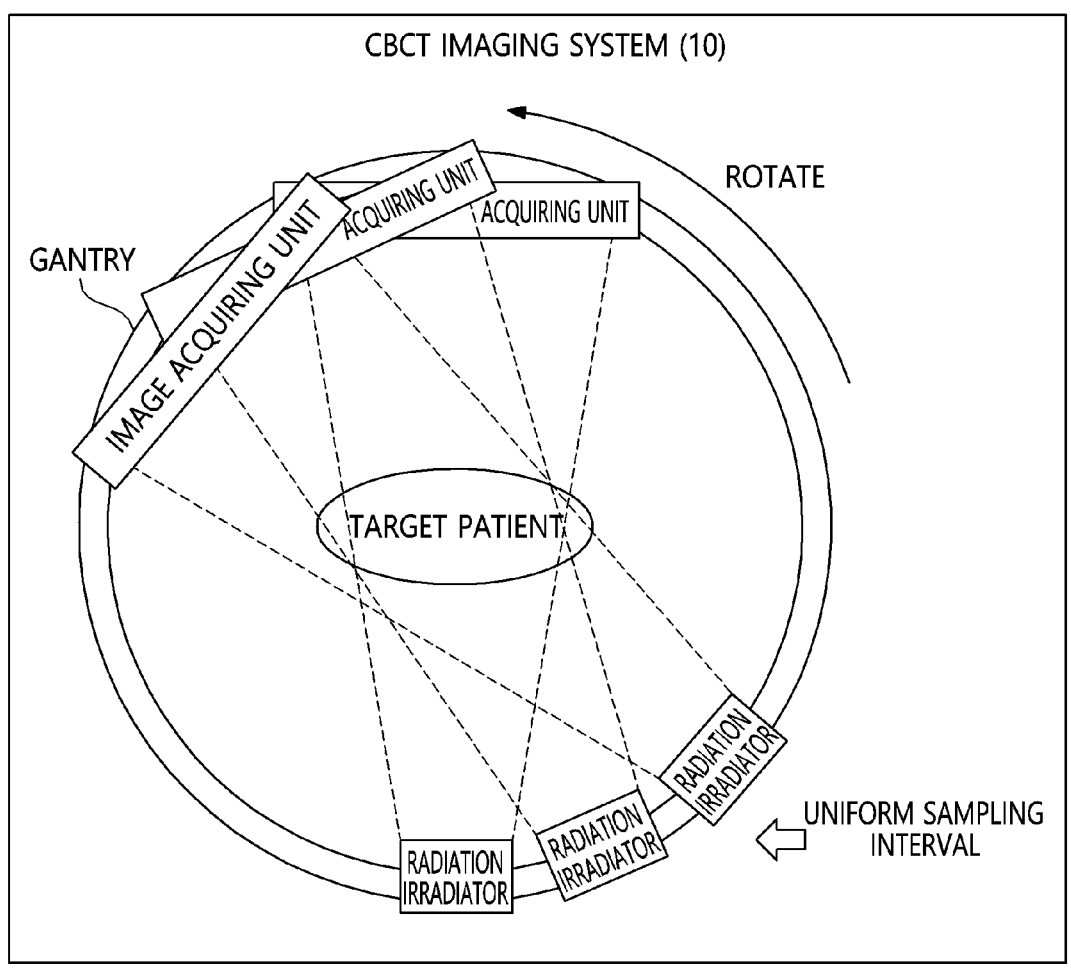
FIG. 1 is a view for explaining an operating process of a CBCT imaging system of the related art.
Figure 2:
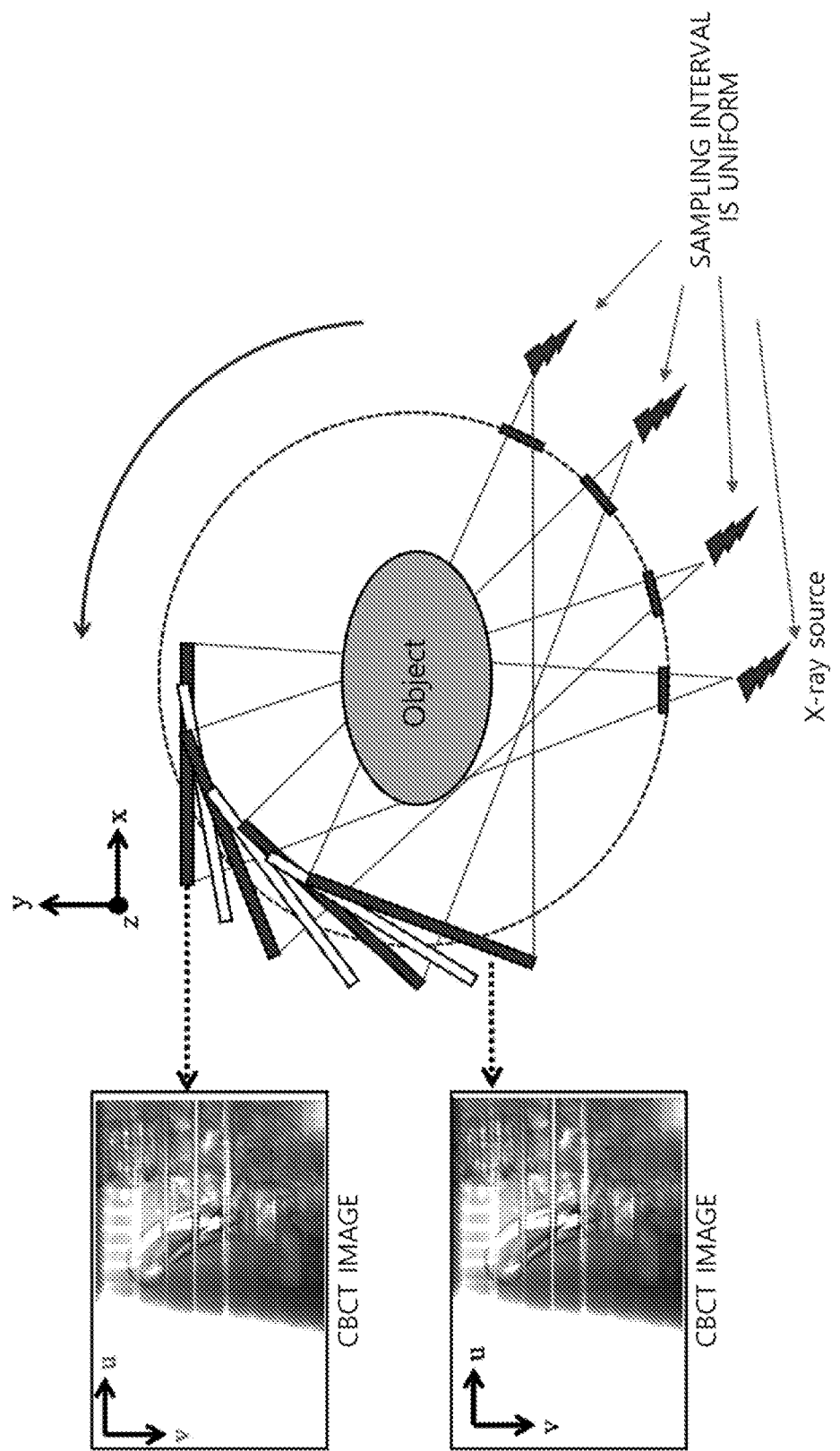
FIG. 2 is a view illustrating an example of the operating process illustrated in FIG. 1.

Hereinafter, embodiments of the present disclosure will be described in detail with reference to the accompanying drawings. Advantages and characteristics of the present disclosure and a method of achieving the advantages and characteristics will be clear by referring to exemplary embodiments described below in detail together with the accompanying drawings. However, the present disclosure is not limited to exemplary embodiments disclosed herein but will be implemented in various different forms. The exemplary embodiments are provided by way of example only so that a person of ordinary skilled in the art can fully understand the disclosures of the present invention and the scope of the present invention. Therefore, the present invention will be defined only by the scope of the appended claims. Like reference numerals generally denote like elements throughout the specification.

Unless otherwise defined, all terms (including technical and scientific terms) used in the present specification may be used as the meaning which may be commonly understood by the person with ordinary skill in the art, to which the present invention belongs. It will be further understood that terms defined in commonly used dictionaries should not be interpreted in an idealized or excessive sense unless expressly and specifically defined.

In the specification, the terms "first" or "second" are used to distinguish one component from the other component so that the scope should not be limited by these terms. For example, a first component may also be referred to as a second component and likewise, the second component may also be referred to as the first component.

In the present specification, in each step, numerical symbols (for example, a, b, and c) are used for the convenience of description, but do not explain the order of the steps so that unless the context apparently indicates a specific order, the order may be different from the order described in the specification. That is, the steps may be performed in the order as described or simultaneously, or an opposite order.

In this specification, the terms "have", "may have", "include", or "may include" represent the presence of the characteristic (for example, a numerical value, a function, an operation, or a component such as a part"), but do not exclude the presence of additional characteristic.

Hereinafter, an exemplary embodiment of a method and an apparatus for acquiring a CBCT image based on adaptive sampling according to the present disclosure will be described in detail with reference to the accompanying drawings.

First, an adaptive sampling based CBCT image acquiring apparatus according to the exemplary embodiment of the present disclosure will be described with reference to FIGS. 3 to 6.

Figure 3:
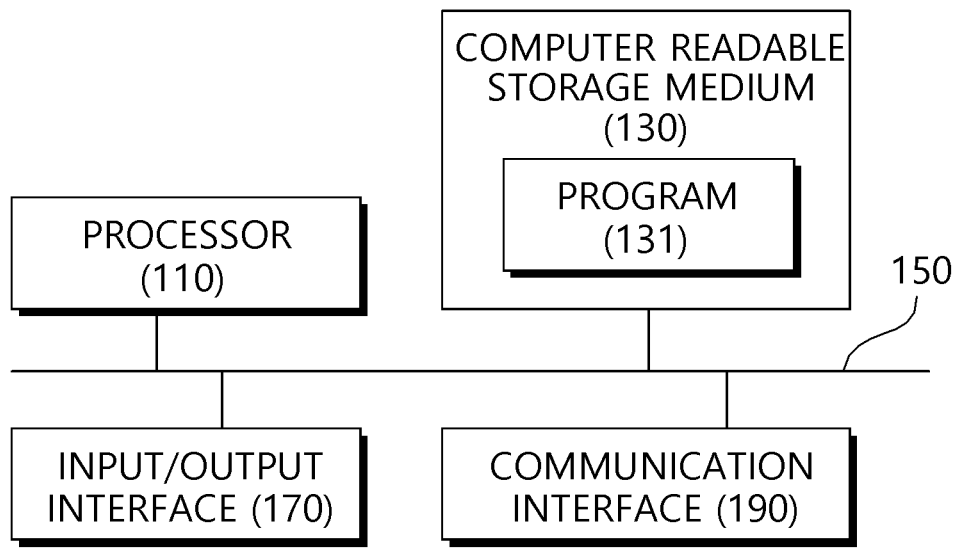
FIG. 3 is a block diagram for explaining an adaptive sampling based CBCT image acquiring apparatus according to an exemplary embodiment of the present disclosure.
Figure 4A:
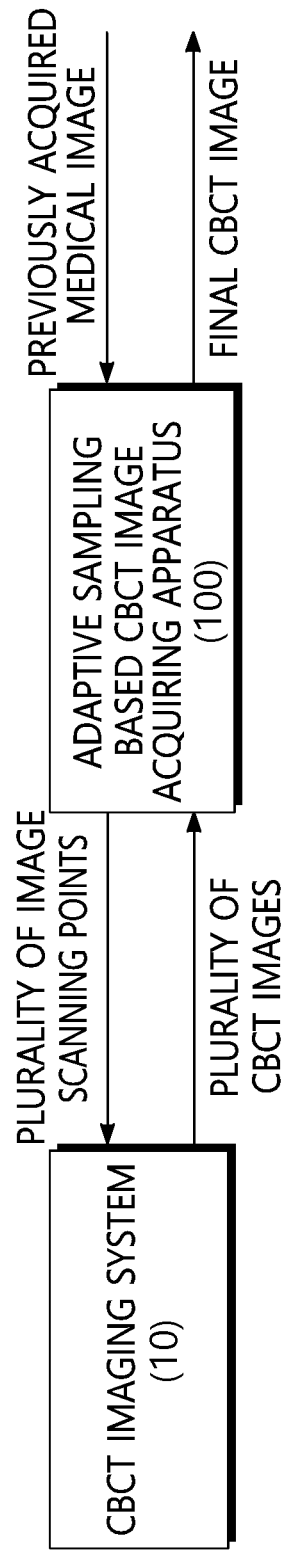
Figure 4B:
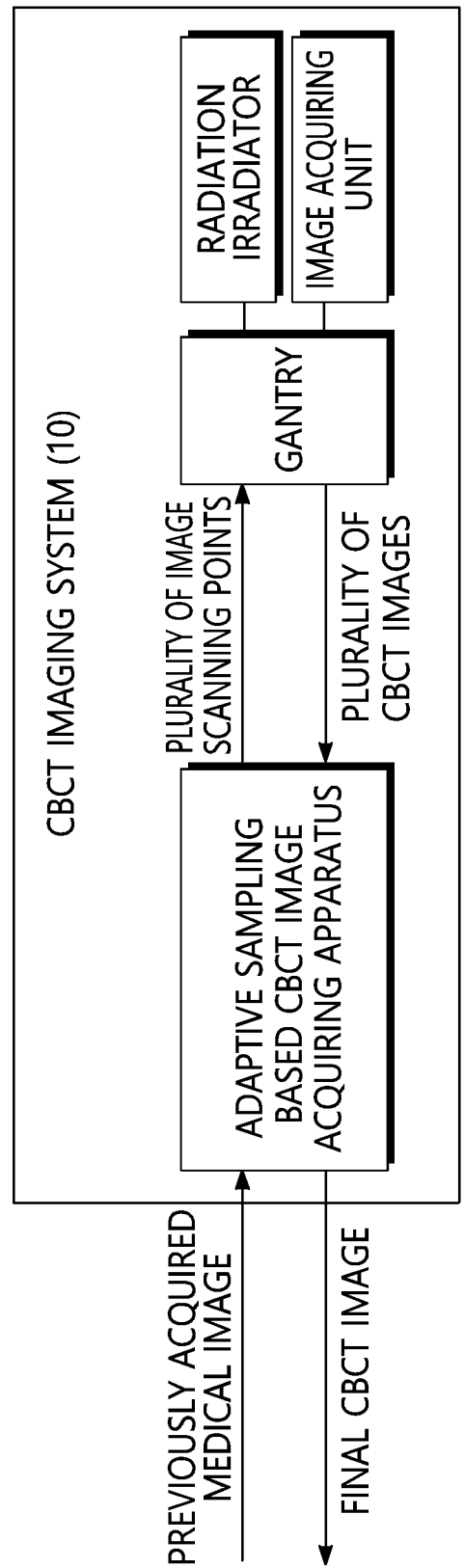
Figure 5:
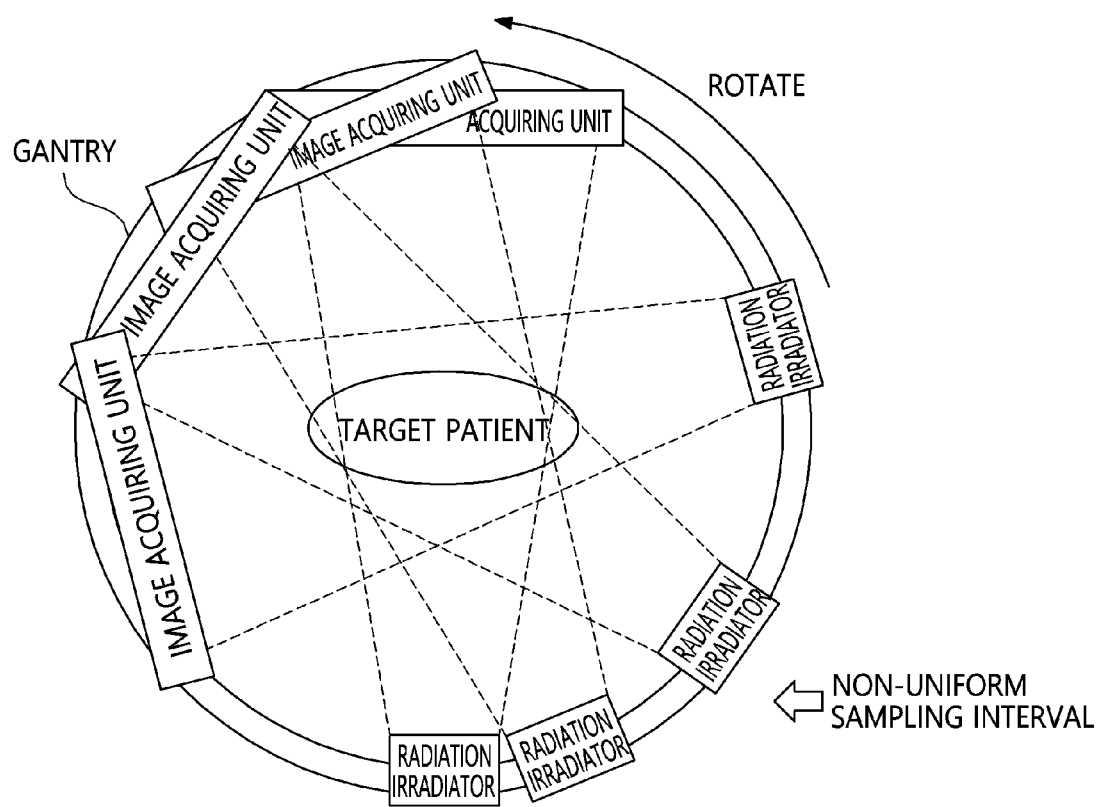
FIG. 5 is a view for explaining an operating process of the CBCT image acquiring apparatus illustrated in FIG. 3.
Figure 6:
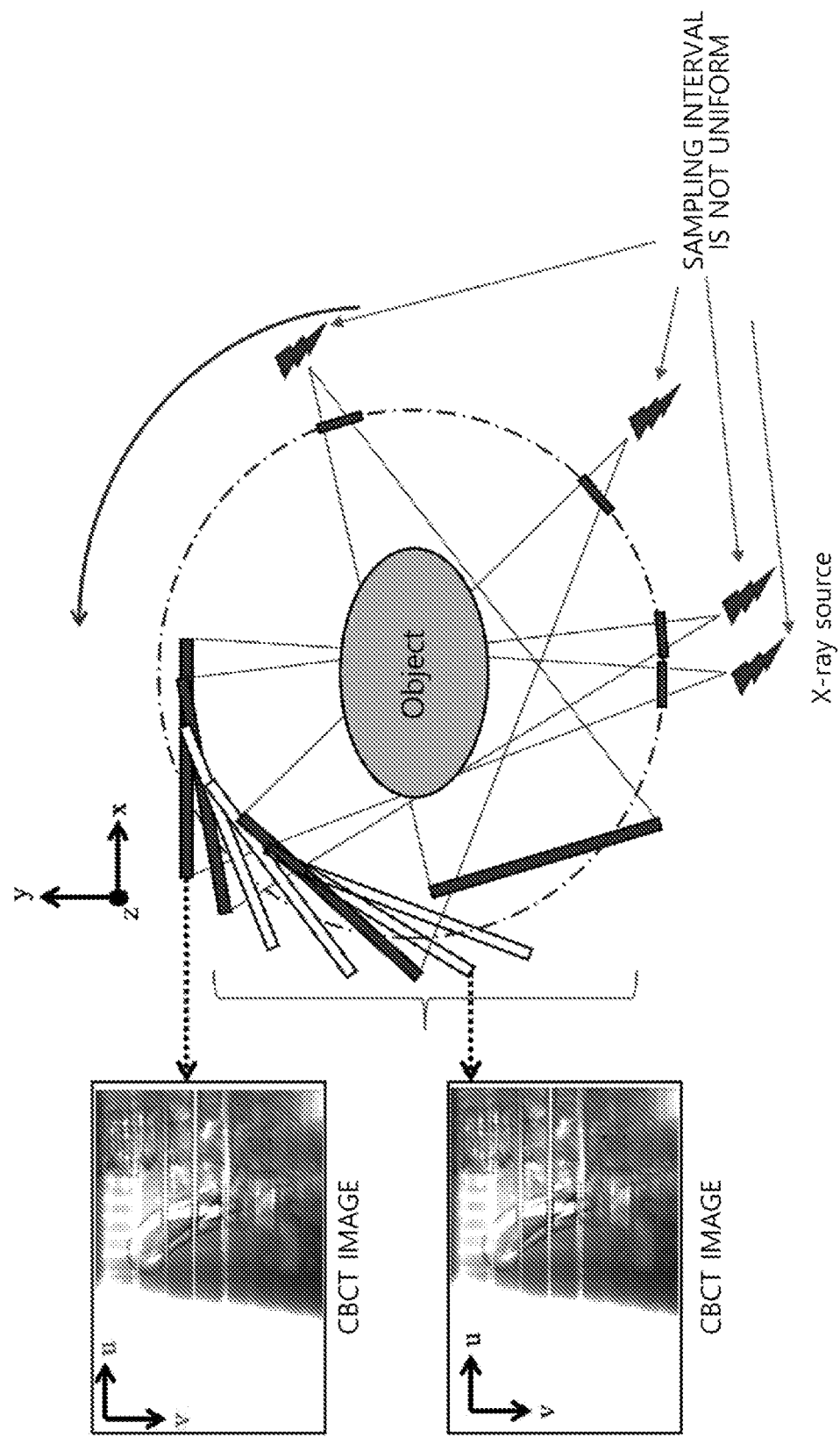
FIG. 6 is a view illustrating an example of the operating process illustrated in FIG. 5.

FIG. 3 is a block diagram for explaining an adaptive sampling based CBCT image acquiring apparatus according to an exemplary embodiment of the present disclosure, FIGS. 4A and 4B are views for explaining an example of implementing the CBCT image acquiring apparatus illustrated in FIG. 3 in which FIG. 4A illustrates that the CBCT image acquiring apparatus and a CBCT imaging system are implemented as independent apparatuses and FIG. 4B illustrates that the CBCT image acquiring apparatus and the CBCT imaging system are integrally implemented, FIG. 5 is a view for explaining an operating process of the CBCT image acquiring apparatus illustrated in FIG. 3, and FIG. 6 is a view illustrating an example of the operating process illustrated in FIG. 5.

Referring to FIG. 3, the adaptive sampling based CBCT image acquiring apparatus 100 according to an exemplary embodiment of the present disclosure (hereinafter, simply referred to as CBCT image acquiring apparatus) reconstructs a plurality of cone beam computed tomography images acquired based on adaptive sampling to acquire a final CBCT image.

Here, the adaptive sampling means that a plurality of CBCT images is acquired by adaptively changing a sampling interval based on a medical image which has been acquired previously for the target patient, rather than a constant sampling interval. The medical image may be a computed tomography volume image and for example, may be a plan CT volume image of the target patient. The medical image may also be a different type of medical image such as a magnetic resonance imaging (MRI) image or a positron emission tomography (PET) image.

That is, the CBCT image acquiring apparatus 100 acquires a plurality of image scanning points based on a medical image which has been acquired previously for the target patient, acquires a plurality of CBCT images for the target patient based on the plurality of image scanning points, and acquires a final CBCT image for the target patient based on the plurality of CBCT images.

Here, the image scanning point may be a gantry rotational index.

To this end, the CBCT image acquiring apparatus 100 may include one or more processors 110, a computer readable storage medium 130, and a communication bus 150.

The processor 110 controls the CBCT image acquiring apparatus 100 to operate. For example, the processor 110 may execute one or more programs 131 stored in the computer readable storage medium 130. One or more programs 131 include one or more computer executable instructions and when the computer executable instruction is executed by the processor 110, the computer executable instruction may be configured to allow the CBCT image acquiring apparatus 100 to perform an operation for acquiring a final CBCT image by reconstructing a plurality of CBCT images acquired based on adaptive sampling.

The computer readable storage medium 130 is configured to store a computer executable instruction or program code, program data and/or other appropriate format of information to acquire a final CBCT image by reconstructing a plurality of CBCT images acquired based on adaptive sampling. The program 131 stored in the computer readable storage medium 130 includes a set of instructions executable by the processor 110. In one exemplary embodiment, the computer readable storage medium 130 may be a memory (a volatile memory such as a random access memory, a non-volatile memory, or an appropriate combination thereof), one or more magnetic disk storage devices, optical disk storage devices, flash memory devices, and another format of storage mediums which is accessed by the CBCT image acquiring apparatus 100 and stores desired information, or an appropriate combination thereof.

The communication bus 150 interconnects various other components of the CBCT image acquiring apparatus 100 including the processor 110 and the computer readable storage medium 130 to each other.

The CBCT image acquiring apparatus 100 may include one or more input/output interfaces 170 and one or more communication interfaces 190 which provide an interface for one or more input/output devices. The input/output interface 170 and the communication interface 190 are connected to the communication bus 150. The input/output device (not illustrated) may be connected to the other components of the CBCT image acquiring apparatus 100 by means of the input/output interface 170.

In the meantime, the CBCT image acquiring apparatus 100 according to the present disclosure may be implemented as an independent apparatus from the CBCT imaging system 10, as illustrated in FIG. 4A. In this case, the CBCT image acquiring apparatus 100 acquires a plurality of image scanning points to scan a CBCT image based on a previously acquired medical image for a target patient and provides the plurality of acquired image scanning points to the CBCT imaging system 10. By doing this, the CBCT imaging system 10 scans the target patient based on the plurality of image scanning points provided from the CBCT image acquiring apparatus 100 to acquire a plurality of CBCT images and provides the plurality of acquired CBCT images to the CBCT image acquiring apparatus 100. The CBCT image acquiring apparatus 100 acquires a final CBCT image for the target patient based on the plurality of CBCT images provided from the CBCT imaging system 100→10.

The CBCT image acquiring apparatus 100 according to the present disclosure may also be implemented to be integrated with the CBCT imaging system 10, as illustrated in FIG. 4B. In this case, the CBCT image acquiring apparatus 100 is implemented in the form of hardware or software to be mounted on the CBCT imaging system 10.

In other words, the CBCT image acquiring apparatus 100 according to the present disclosure may acquire a plurality of CBCT images for the target patient while rotating the gantry at non-uniform sampling intervals. That is, the CBCT image acquiring apparatus 100 may acquire a plurality of CBCT images by non-uniform sampling.

In this case, the CBCT image acquiring apparatus 100 acquires a plurality of image scanning points to scan a CBCT image using a previously acquired medical image for the target patient and scans the target patient at the plurality of acquired image scanning points to acquire a plurality of CBCT images. As described above, the CBCT image acquiring apparatus 100 performs the CBCT scanning in a sampling position determined based on a past medical image of the target patient to acquire a plurality of CBCT images with non-uniform sampling intervals.

Now, a CBCT image acquiring method based on adaptive sampling according to the exemplary embodiment of the present disclosure will be described with reference to FIGS. 7 to 12.

Figure 7:
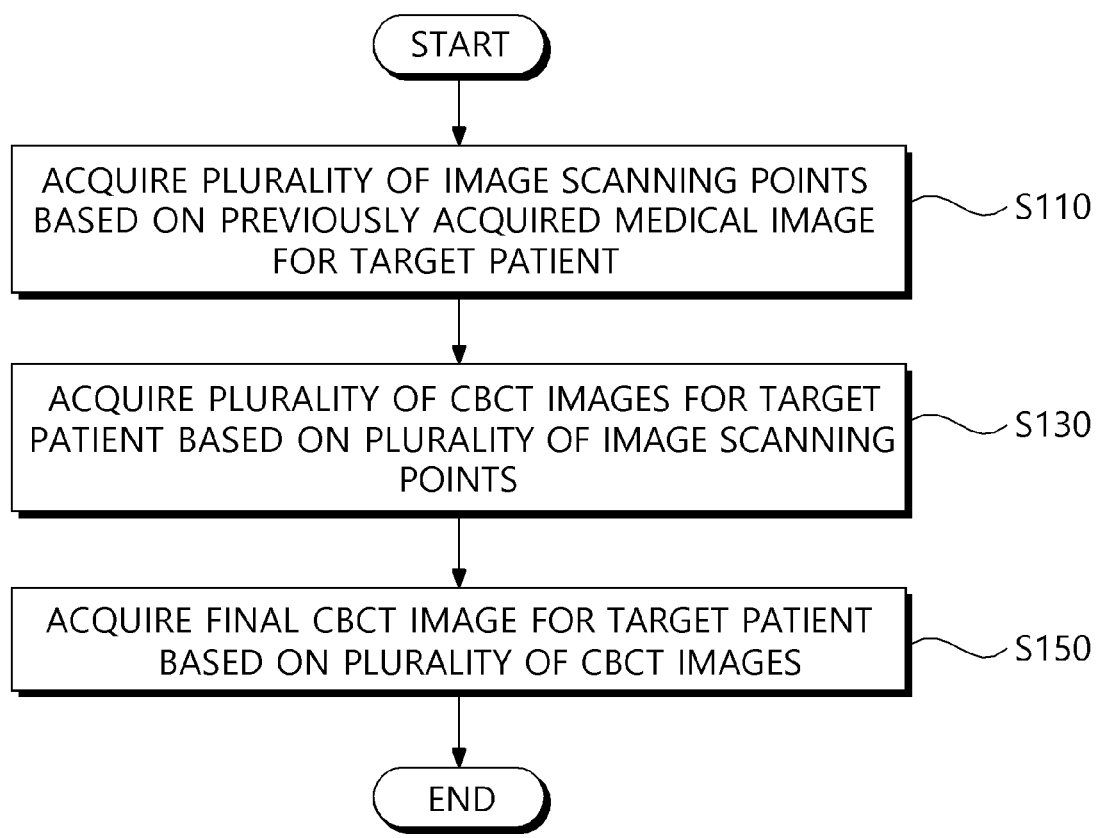
FIG. 7 is a flowchart for explaining an adaptive sampling based CBCT image acquiring method according to an exemplary embodiment of the present disclosure.
Figure 8:
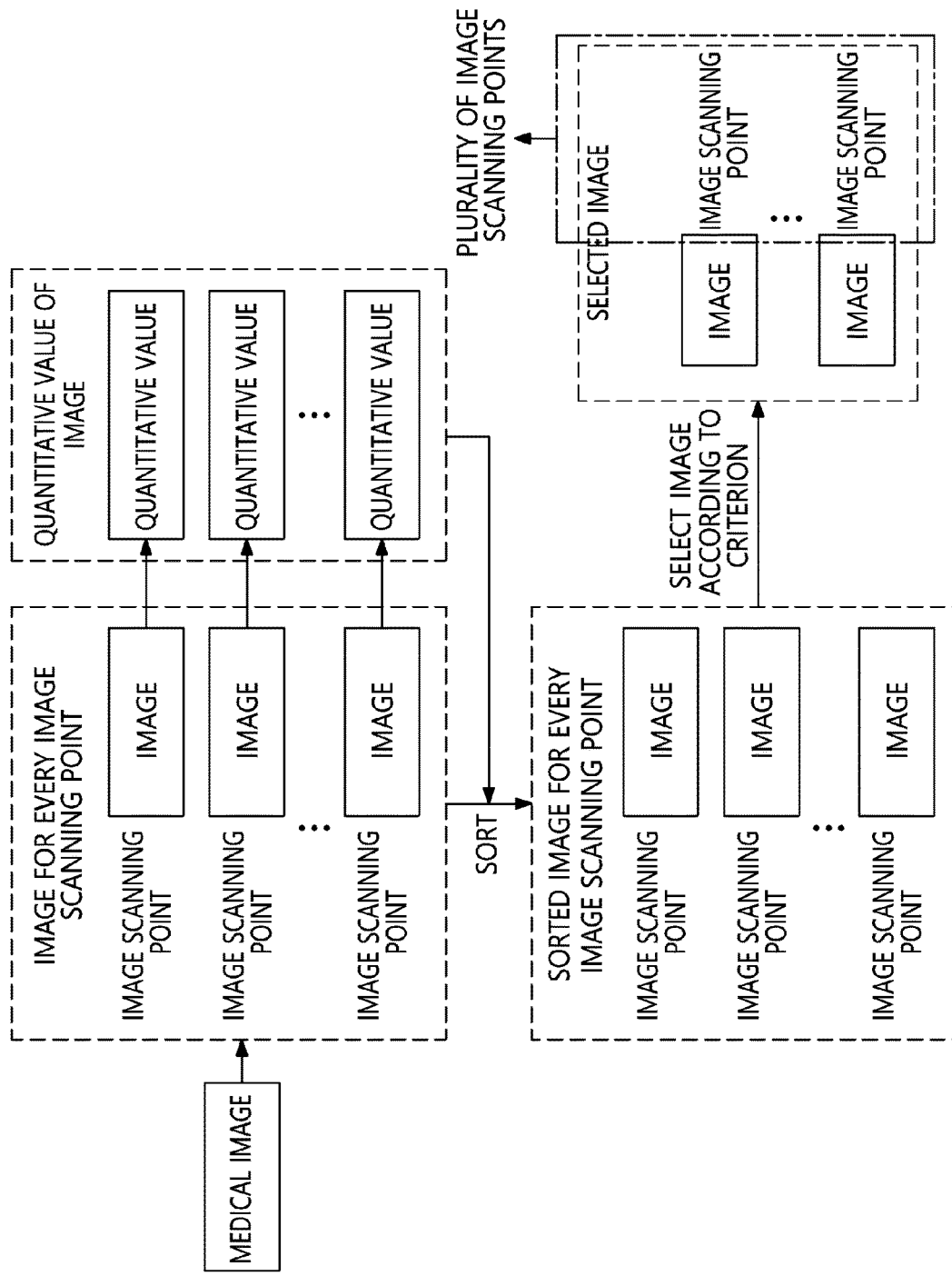
FIG. 8 is a view for explaining a detailed process of a step of acquiring a plurality of image scanning points illustrated in FIG. 7.
Figure 9:
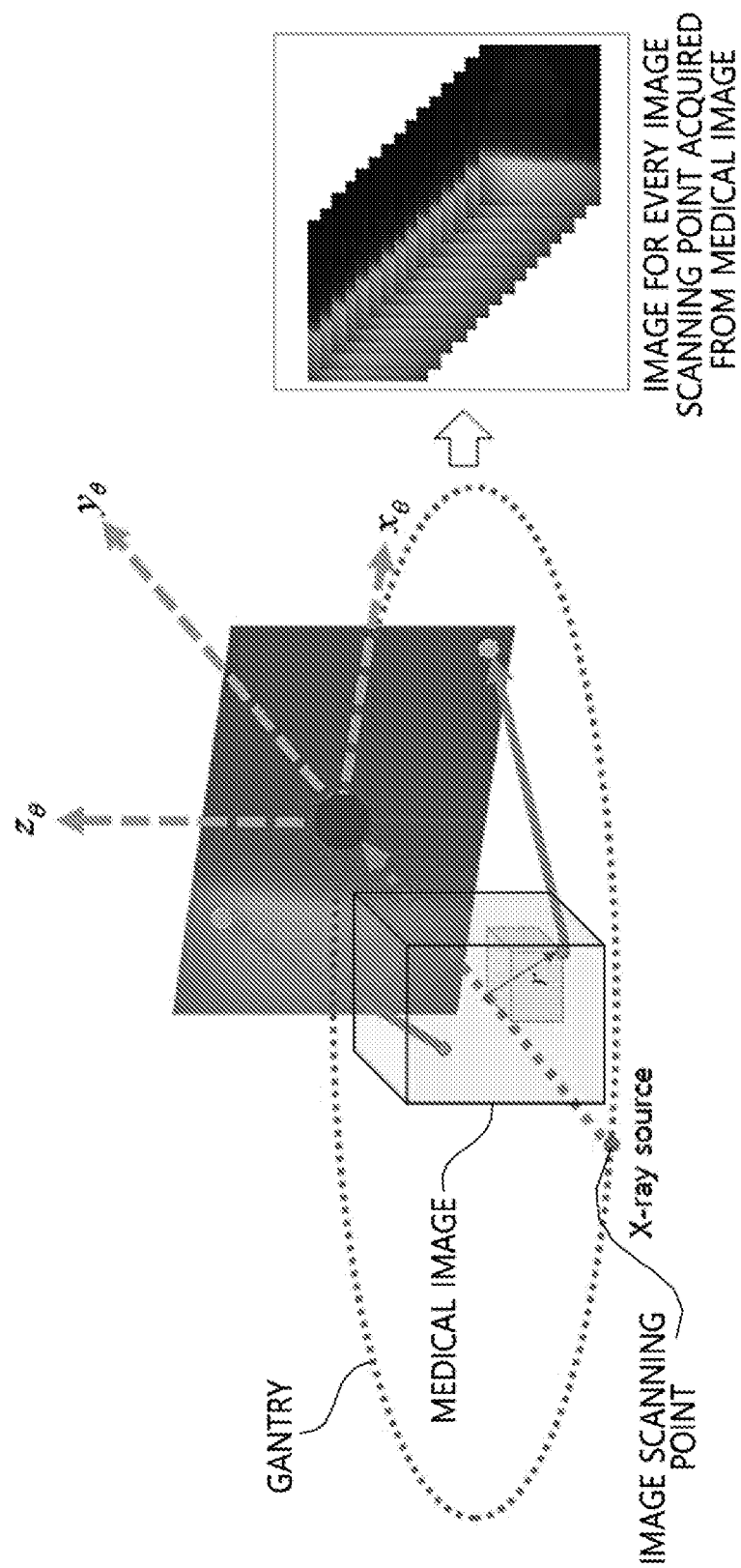
FIG. 9 is a view for explaining a process of acquiring an image for every image scanning point illustrated in FIG. 7.
Figure 10:
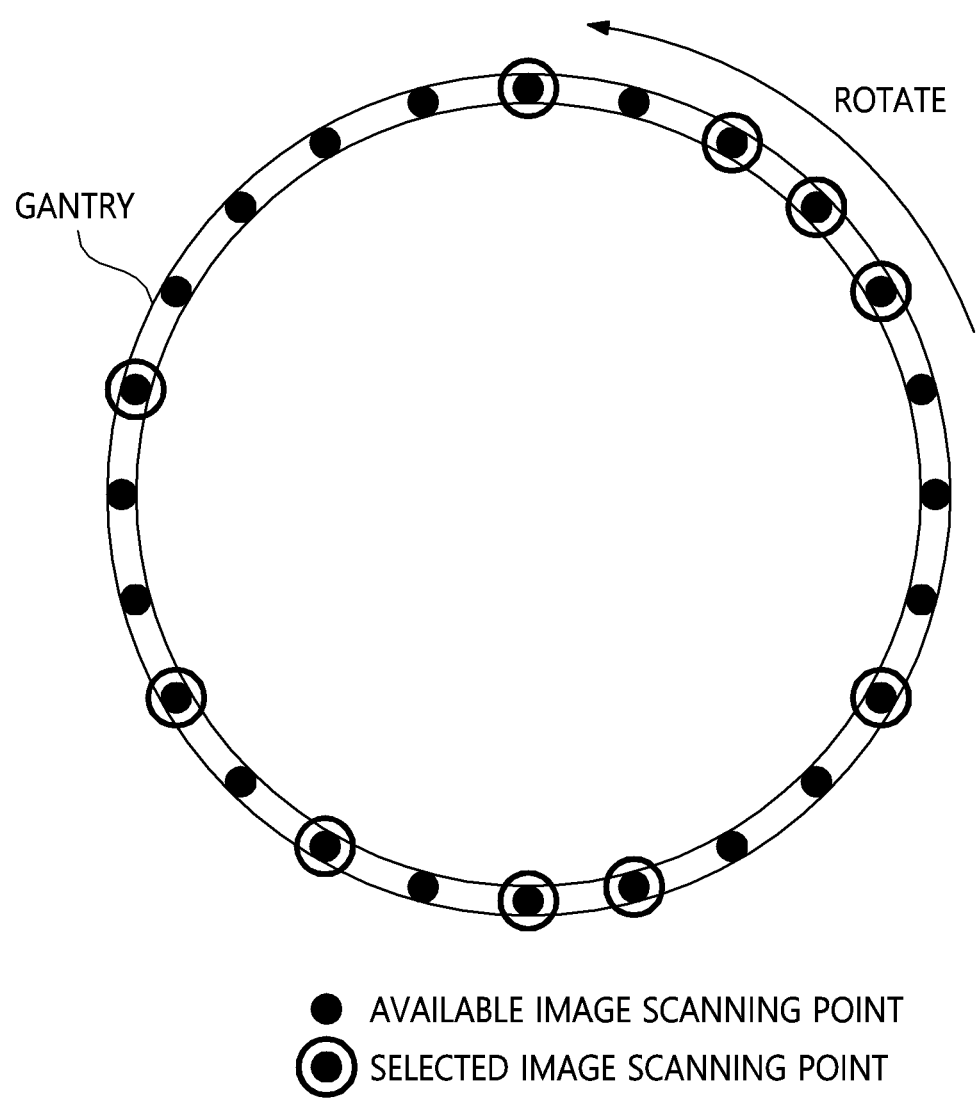
FIG. 10 is a view for explaining an example of a process of acquiring a plurality of CBCT images based on adaptive sampling according to an exemplary embodiment of the present disclosure.
Figure 11:
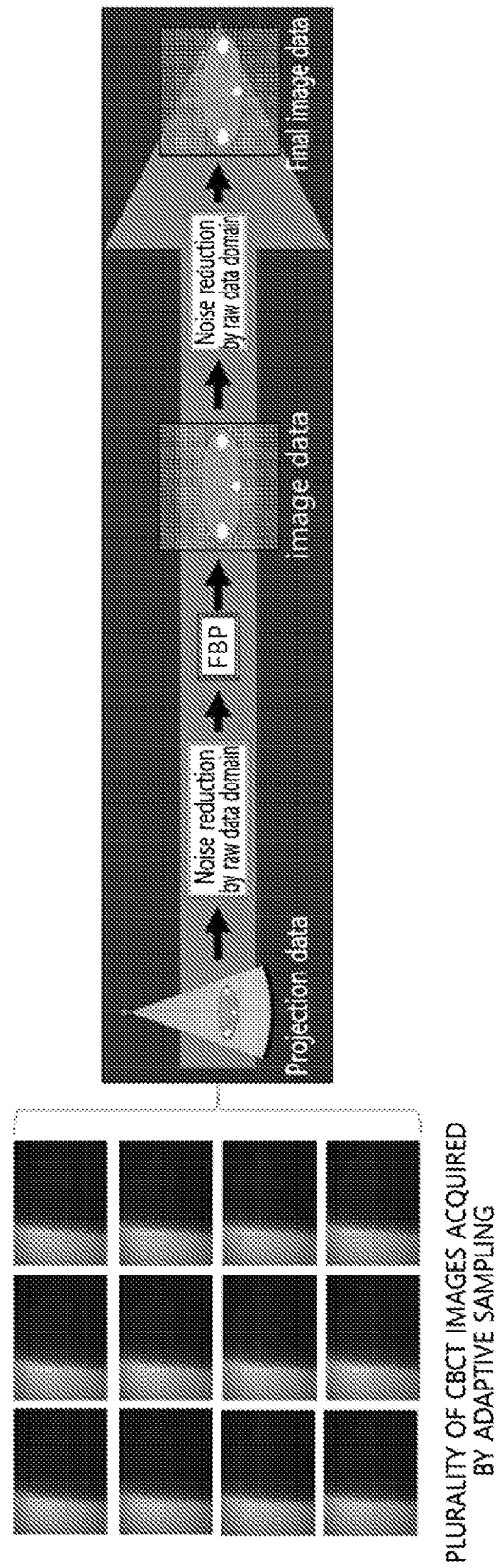
FIG. 11 is a view for explaining a detailed process of a process of acquiring a final CBCT image illustrated in FIG. 7 using an analytical reconstruction algorithm.
Figure 12:
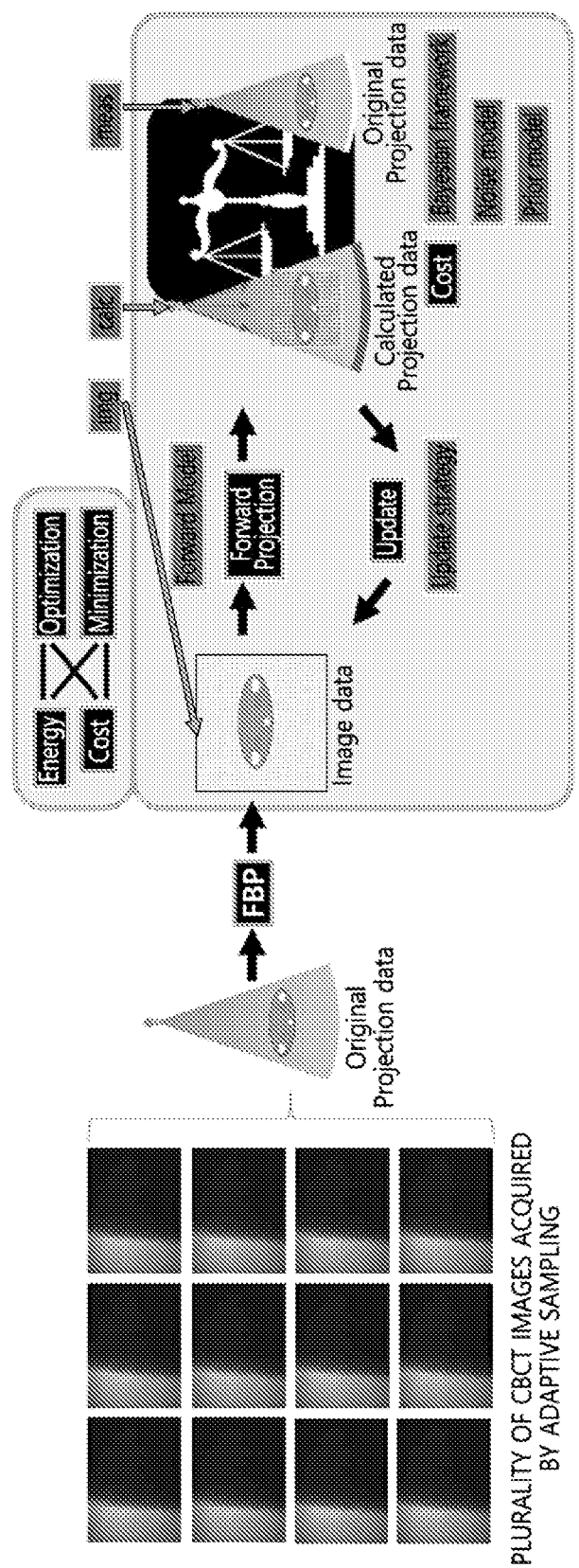
FIG. 12 is a view for explaining a detailed process of a process of acquiring a final CBCT image illustrated in FIG. 7 using an iterative reconstruction algorithm.

FIG. 7 is a flowchart for explaining an adaptive sampling based CBCT image acquiring method according to an exemplary embodiment of the present disclosure, FIG. 8 is a view for explaining a detailed process of a step of acquiring a plurality of image scanning points illustrated in FIG. 7, FIG. 9 is a view for explaining a process of acquiring an image for every image scanning point illustrated in FIG. 7, FIG. 10 is a view for explaining an example of a process of acquiring a plurality of CBCT images based on adaptive sampling according to an exemplary embodiment of the present disclosure, FIG. 11 is a view for explaining a detailed process of a process of acquiring a final CBCT image illustrated in FIG. 7 using an analytical reconstruction algorithm, and FIG. 12 is a view for explaining a detailed process of a process of acquiring a final CBCT image illustrated in FIG. 7 using an iterative reconstruction algorithm.

Referring to FIG. 7, the processor 100 of the CBCT image acquiring apparatus 100 acquires a plurality of image scanning points based on a previously acquired medical image for a target patient in step S110.

That is, the processor 110 may acquire an image for every image scanning point based on a previously scanned medical image for the target patient, as illustrated in FIG. 8.

At this time, the processor 110, as illustrated in FIG. 9, acquires the image for every image scanning point from the medical image by means of forward projection, using geometric information of the CBCT imaging system 10.

As illustrated in FIG. 8, the processor 110 acquires a quantitative value for each of acquired images for image scanning points and sorts the images for image scanning points based on the quantitative value for each of images for image scanning points.

For example, the processor 110 sorts the images for image scanning points in a descending order based on the quantitative value for each of acquired images for image scanning points.

At this time, the processor 110 sorts the images for image scanning points based on an entropy for each of acquired images for image scanning points. Here, the entropy measures a randomness of the system or a degree of disorder. The higher the disorder, the higher the entropy and the lower the disorder, the lower the entropy and the entropy may be calculated by the following Equations 1 and 2. The entropy for the image is calculated by the well-known technique of the related art so that a detailed description will be omitted.

$$H = -\sum_i PDF(i) \log PDF(i) \quad \text{[Equation 1]}$$

$$p(i) = PDF(i) = \frac{\text{histogram }(x_i)}{\text{Total Number}} \quad \text{[Equation 2]}$$

Here, H denotes an entropy. PDF(i) denotes a probability density function (PDF) for a random variable i.

Further, the processor 110 sorts the images for image scanning points based on a radiomic feature for each of acquired images for image scanning points. Here, the radiomic feature is classified into a plurality of classes as follows, according to a type, and is configured by a plurality of features for every class. That is, the processor 110 may acquire a quantitative value for each of images for image scanning points using at least one feature among a plurality of features according to the radiomic feature. Features of only some classes of the radiomic feature will be described below, but features of the other class may also be used. The radiomic feature for the image is calculated by the well-known technique of the related art so that a detailed description will be omitted.

Class: 2D Shape Features

Features of a 2D shape feature class are features for 2D size and shape of a region of interest (ROI) and specific features are as follows.

1. Mesh Surface Feature $$A_i = \frac{1}{2} Oa_i \times Ob_i \quad \text{[Equation 3]}$$

$$A = \sum_{i=1}^{N_f} A_i$$

2. Pixel Surface Feature $$A_{pixel} = \sum_{k=1}^{N_v} A_k \quad \text{[Equation 4]}$$

3. Perimeter Feature $$P_i = \sqrt{(a_i - b_i)^2} \quad \text{[Equation 5]}$$

$$P = \sum_{i=1}^{N_f} P_i$$

4. Perimeter to Surface ratio Feature $$\text{perimeter to surface ratio} = \frac{P}{A} \quad \text{[Equation 6]}$$

5. Sphericity Feature $$\text{sphericity} = \frac{2\pi R}{P} = \frac{2\sqrt{\pi A}}{P} \quad \text{[Equation 7]}$$

6. Spherical Disproportion Feature $$\text{spherical disproportion} = \frac{P}{2\sqrt{\pi A}} \quad \text{[Equation 8]}$$

7. Maximum 2D Diameter Feature

A maximum diameter is defined as an Euclidean distance of a largest pair between tumor surface mesh vertices.

8. Major Axis Length Feature $$\text{major axis} = 4\sqrt{\lambda_{major}} \quad \text{[Equation 9]}$$

9. Minor Axis Length Feature $$\text{minor axis} = 4\sqrt{\lambda_{minor}} \quad \text{[Equation 10]}$$

10. Elongation Feature $$\text{elongation} = \sqrt{\frac{\lambda_{minor}}{\lambda_{major}}} \quad \text{[Equation 11]}$$

Class: Gray Level Co-occurrence Matrix (GLCM) Features

Features of GLCM feature class are features for a second-order joint probability function of an image region restricted by a mask and specific features are as follows.

1. Autocorrelation Feature $$\text{autocorrelation} = \sum_{i=1}^{N_g} \sum_{j=1}^{N_g} p(i, j) ij \quad \text{[Equation 12]}$$

2. Joint Average Feature $$\text{joint average} = \mu_x = \sum_{i=1}^{N_g} \sum_{j=1}^{N_g} p(i, j) i \quad \text{[Equation 13]}$$

3. Cluster Prominence Feature $$\text{cluster prominence} = \sum_{i=1}^{N_g} \sum_{j=1}^{N_g} (i + j - \mu_x - \mu_y)^4 p(i, j) \quad \text{[Equation 14]}$$

4. Cluster Shade Feature $$\text{cluster shade} = \sum_{i=1}^{N_g}\sum_{j=1}^{N_g}(i+j-\mu_x-\mu_y)^3 p(i,j) \quad \text{[Equation 15]}$$

5. Cluster Tendency Feature $$\text{cluster tendency} = \sum_{i=1}^{N_g}\sum_{j=1}^{N_g}(i+j-\mu_x-\mu_y)^2 p(i,j) \quad \text{[Equation 16]}$$

6. Contrast Feature $$\text{contrast} = \sum_{i=1}^{N_g}\sum_{j=1}^{N_g}(i-j)^2 p(i,j) \quad \text{[Equation 17]}$$

7. Correlation Feature $$\text{correlation} = \frac{\sum_{i=1}^{N_g}\sum_{j=1}^{N_g} p(i,j)ij - \mu_x\mu_y}{\sigma_x(i)\sigma_y(j)} \quad \text{[Equation 18]}$$

8. Difference Average Feature $$\text{difference average} = \sum_{k=0}^{N_g-1} k p_{x-y}(k) \quad \text{[Equation 19]}$$

9. Difference Entropy Feature $$\text{difference entropy} = \sum_{k=0}^{N_g-1} p_{x-y}(k) \log_2(p_{x-y}(k) + \varepsilon) \quad \text{[Equation 20]}$$

10. Difference Variance Feature $$\text{difference variance} = \sum_{k=0}^{N_g-1}(k-DA)^2 p_{x-y}(k) \quad \text{[Equation 21]}$$

11. Joint Energy Feature $$\text{joint energy} = \sum_{i=1}^{N_g}\sum_{j=1}^{N_g}(p(i,j))^2 \quad \text{[Equation 22]}$$

12. Joint Entropy Feature $$\text{joint entropy} = -\sum_{i=1}^{N_g}\sum_{j=1}^{N_g} p(i,j) \log_2(p(i,j) + \varepsilon) \quad \text{[Equation 23]}$$

13. Informational Measure of Correlation (IMC) 1 Feature $$IMC1 = \frac{HXY - HXY1}{\max\{HX, HY\}} \quad \text{[Equation 24]}$$

14. Informational Measure of Correlation (IMC) 2 Feature $$IMC2 = \sqrt{1 - e^{-2(HXY2 - HXY)}} \quad \text{[Equation 25]}$$

15. Inverse Difference Moment (IDM) Feature $$IDM = \sum_{k=0}^{N_g-1} \frac{p_{x-y}(k)}{1+k^2} \quad \text{[Equation 26]}$$

16. Maximal Correlation Coefficient (MCC) Feature $$MCC = \sqrt{\text{second largest eigenvalue of } Q} \quad \text{[Equation 27]}$$

$$Q(i,j) = \sum_{k=0}^{N_g} \frac{p(i,k)p(j,k)}{p_x(i)p_y(k)}$$

17. Inverse Difference Moment Normalized (IDMN) Feature $$IDMN = \sum_{k=0}^{N_g-1} \frac{p_{x-y}(k)}{1 + \left(\frac{k^2}{N_g^2}\right)} \quad \text{[Equation 28]}$$

18. Inverse Difference (ID) Feature $$ID = \sum_{k=0}^{N_g-1} \frac{p_{x-y}(k)}{1+k} \quad \text{[Equation 29]}$$

19. Inverse Difference Normalized (IDN) Feature $$IDN = \sum_{k=0}^{N_g-1} \frac{p_{x-y}(k)}{1 + \left(\frac{k}{N_g}\right)} \quad \text{[Equation 30]}$$

20. Inverse Variance Feature $$\text{inverse variance} = \sum_{k=1}^{N_g-1} \frac{p_{x-y}(k)}{k^2} \quad \text{[Equation 31]}$$

21. Maximum Probability Feature $$\text{maximum probability} = \max(p(i,j)) \quad \text{[Equation 32]}$$

22. Sum Average Feature $$\text{sum average} = \sum_{k=2}^{2N_g} p_{x+y}(k) k \quad \text{[Equation 33]}$$

23. Sum Entropy Feature $$\text{sum entropy} = \sum_{k=2}^{2N_g} p_{x+y}(k)\log_2(p_{x+y}(k) + \varepsilon) \qquad \text{[Equation 34]}$$

24. Sum of Squares Feature $$\text{sum squares} = \sum_{i=1}^{N_g}\sum_{j=1}^{N_g}(i-\mu_x)^2 p(i,j) \qquad \text{[Equation 35]}$$

Class: Gray Level Size Zone Matrix (GLSZM) Features

Features of GLSZM feature class are features for quantification of a gray level zone in an image and specific features are as follows.

1. Small Area Emphasis (SAE) Feature $$SAE = \frac{\sum_{i=1}^{N_g}\sum_{j=1}^{N_s}\frac{P(i,j)}{j^2}}{N_z} \qquad \text{[Equation 36]}$$

2. Large Area Emphasis (LAE) Feature $$LAE = \frac{\sum_{i=1}^{N_g}\sum_{j=1}^{N_s}P(i,j)j^2}{N_z} \qquad \text{[Equation 37]}$$

3. Gray Level Non-Uniformity (GLN) Feature $$GLN = \frac{\sum_{i=1}^{N_g}\left(\sum_{j=1}^{N_s}P(i,j)\right)^2}{N_z} \qquad \text{[Equation 38]}$$

4. Gray Level Non-Uniformity Normalized (GLNN) Feature $$GLNN = \frac{\sum_{i=1}^{N_g}\left(\sum_{j=1}^{N_s}P(i,j)\right)^2}{N_z^2} \qquad \text{[Equation 39]}$$

5. Size-Zone Non-Uniformity (SZN) Feature $$SZN = \frac{\sum_{j=1}^{N_s}\left(\sum_{i=1}^{N_g}P(i,j)\right)^2}{N_z} \qquad \text{[Equation 40]}$$

6. Side-Zone Non-Uniformity Normalized (SZNN) Feature $$SZNN = \frac{\sum_{j=1}^{N_s}\left(\sum_{i=1}^{N_g}P(ij)\right)^2}{N_z^2} \qquad \text{[Equation 41]}$$

7. Zone Percentage (ZP) Feature $$ZP = \frac{N_z}{N_p} \qquad \text{[Equation 42]}$$

8. Grey Level Variance (GLV) Feature $$GLV = \sum_{i=1}^{N_g}\sum_{j=1}^{N_s}p(i,j)(i-\mu)^2 \qquad \text{[Equation 43]}$$

9. Zone Variance (ZV) Feature $$ZV = \sum_{i=1}^{N_g}\sum_{j=1}^{N_s}p(i,j)(j-\mu)^2 \qquad \text{[Equation 44]}$$

10. Zone Entropy (ZE) Feature $$ZE = \sum_{i=1}^{N_g}\sum_{j=1}^{N_s}p(i,j)\log_2(p(i,j)+\varepsilon) \qquad \text{[Equation 45]}$$

11. Low Gray Level Zone Emphasis (LGLZE) Feature $$LGLZE = \frac{\sum_{i=1}^{N_g}\sum_{j=1}^{N_s}\frac{P(i,j)}{i^2}}{N_z} \qquad \text{[Equation 46]}$$

12. High Gray Level Zone Emphasis (HGLZE) Feature $$HGLZE = \frac{\sum_{i=1}^{N_g}\sum_{j=1}^{N_s}P(i,j)i^2}{N_z} \qquad \text{[Equation 47]}$$

13. Small Area Low Gray Level Emphasis (SALGLE) Feature $$SALGLE = \frac{\sum_{i=1}^{N_g}\sum_{j=1}^{N_s}\frac{P(i,j)}{i^2 j^2}}{N_z} \qquad \text{[Equation 48]}$$

14. Small Area High Gray Level Emphasis (SAHGLE) Feature $$SAHGLE = \frac{\sum_{i=1}^{N_g}\sum_{j=1}^{N_s}\frac{P(i,j)i^2}{j^2}}{N_z}$$ [Equation 49]

15. Large Area Low Gray Level Emphasis (LALGLE) Feature $$LALGLE = \frac{\sum_{i=1}^{N_g}\sum_{j=1}^{N_s}\frac{P(i,j)j^2}{i^2}}{N_z}$$ [Equation 50]

16. Large Area High Gray Level Emphasis (LAHGLE) Feature $$LAHGLE = \frac{\sum_{i=1}^{N_g}\sum_{j=1}^{N_s}P(i,j)i^2j^2}{N_z}$$ [Equation 51]

Class: Gray Level Run Length Matrix (GLRLM) Features

Features of GLRLM feature class are features for quantification of a gray level run defined by a pixel number of consecutive pixels having the same gray level value and specific features are as follows.

1. Short Run Emphasis (SRE) Feature $$SRE = \frac{\sum_{i=1}^{N_g}\sum_{j=1}^{N_\gamma}\frac{P(i,j|\theta)}{j^2}}{N_r(\theta)}$$ [Equation 52]

2. Long Run Emphasis (LRE) Feature $$LRE = \frac{\sum_{i=1}^{N_g}\sum_{j=1}^{N_\gamma}P(i,j|\theta)j^2}{N_r(\theta)}$$ [Equation 53]

3. Gray Level Non-Uniformity (GLN) Feature $$GLN = \frac{\sum_{i=1}^{N_g}\left(\sum_{j=1}^{N_\gamma}P(i,j|\theta)\right)^2}{N_r(\theta)}$$ [Equation 54]

4. Gray Level Non-Uniformity Normalized (GLNN) Feature $$GLNN = \frac{\sum_{i=1}^{N_g}\left(\sum_{j=1}^{N_\gamma}P(i,j|\theta)\right)^2}{N_r(\theta)^2}$$ [Equation 55]

5. Run Length Non-Uniformity (RLN) Feature $$RLN = \frac{\sum_{j=1}^{N_\gamma}\left(\sum_{i=1}^{N_g}P(i,j|\theta)\right)^2}{N_r(\theta)}$$ [Equation 56]

6. Run Length Non-Uniformity Normalized (RLNN) Feature $$RLNN = \frac{\sum_{j=1}^{N_\gamma}\left(\sum_{i=1}^{N_g}P(i,j|\theta)\right)^2}{N_r(\theta)^2}$$ [Equation 57]

7. Run Percentage (RP) Feature $$RP = \frac{N_r(\theta)}{N_p}$$ [Equation 58]

8. Grey Level Variance (GLV) Feature $$GLV = \sum_{i=1}^{N_g}\sum_{j=1}^{N_\gamma}(i,j|\theta)(i-\mu)^2$$ [Equation 59]

9. Run Variance (RV) Feature $$RV = \sum_{i=1}^{N_g}\sum_{j=1}^{N_\gamma}p(i,j|\theta)(j-\mu)^2$$ [Equation 60]

10. Run Entropy (RE) Feature $$RE = -\sum_{i=1}^{N_g}\sum_{j=1}^{N_\gamma}p(i,j|\theta)\log_2(p(i,j|\theta)+\varepsilon)$$ [Equation 61]

11. Low Gray Level Run Emphasis (LGLRE) Feature $$LGLRE = \frac{\sum_{i=1}^{N_g}\sum_{j=1}^{N_\gamma}\frac{P(i,j|\theta)}{i^2}}{N_r(\theta)}$$ [Equation 62]

12. High Gray Level Run Emphasis (HGLRE) Feature $$HGLRE = \frac{\sum_{i=1}^{N_g}\sum_{j=1}^{N_\gamma}P(i,j|\theta)i^2}{N_r(\theta)}$$ [Equation 63]

13. Short Run Low Gray Level Emphasis (SRLGLE) Feature $$SRLGLE = \frac{\sum_{i=1}^{N_g}\sum_{j=1}^{N_\gamma}\frac{P(i,j|\theta)}{i^2 j^2}}{N_r(\theta)} \quad \text{[Equation 64]}$$

14. Short Run High Gray Level Emphasis (SRHGLE) Feature $$SRHGLE = \frac{\sum_{i=1}^{N_g}\sum_{j=1}^{N_\gamma}\frac{P(i,j|\theta)i^2}{j^2}}{N_r(\theta)} \quad \text{[Equation 65]}$$

15. Long Run Low Gray Level Emphasis (LRLGLE) Feature $$LRLGLE = \frac{\sum_{i=1}^{N_g}\sum_{j=1}^{N_\gamma}\frac{P(i,j|\theta)j^2}{i^2}}{N_r(\theta)} \quad \text{[Equation 66]}$$

16. Long Run High Gray Level Emphasis (LRHGLE) Feature $$LRHGLE = \frac{\sum_{i=1}^{N_g}\sum_{j=1}^{N_\gamma}P(i,j|\theta)i^2 j^2}{N_r(\theta)} \quad \text{[Equation 67]}$$

The quantitative value may also use another measurement index (another method for calculating a quantitative value corresponding to the input image) other than the entropy or the radiomic feature.

In the meantime, the processor 110 may acquire a quantitative value for each of images for image scanning points with respect to an entire area of the acquired image for every image scanning point. The processor 110 may also acquire a quantitative value for each of images for image scanning points with respect to a partial area of the acquired image for every image scanning point. For example, during a radiation therapy, a CT scan is performed for a patient plan before CBCT and users contour organs of interest for the plan on the acquired CT image. In this case, a quantitative value for each of acquired images for image scanning points may be acquired with respect to the contoured area.

As illustrated in FIG. 8, the processor 110 selects a plurality of images according to a predetermined criterion, among sorted images for image scanning points.

For example, the processor 110 may select a plurality of images in the order of larger quantitative values, among the sorted images for image scanning points. Here, the number of selected images may be set in advance as a specific number (for example, 10). Further, the number of selected images may be determined by a predetermined ratio (for example, 30%) with respect to a number of entire image scanning points. When the number of entire image scanning points is 20 and a predetermined ratio is 25%, the number of selected images may be 5 (=20*25%).

Further, when the predetermined criterion is "an image having a quantitative value which is equal to or larger than a predetermined threshold", the processor 110 selects images having a quantitative value corresponding to the image which is larger than a predetermined threshold value, among the sorted images for image scanning points.

As illustrated in FIG. 8, the processor 110 acquires image scanning points corresponding to the plurality of selected images as the plurality of image scanning points.

Next, the processor 110 acquires a plurality of CBCT images for the target patient based on the plurality of image scanning points in step S130.

That is, the processor 110 scans the target patient at each of the plurality of image scanning points using the CBCT imaging system 10 to acquire a plurality of CBCT images.

For example, referring to FIG. 10, the processor 110 scans the target patient at each of image scanning points (selected image scanning points of FIG. 10) selected based on the past medical image of the target patient, among all the image scanning points (available image scanning points of FIG. 10) to acquire a plurality of CBCT images. That is, the radiation irradiator of the CBCT scanning system 10 irradiates the radiation beam toward the target patient at each of the selected image scanning points (selected image scanning points of FIG. 10) and the image acquiring unit of the CBCT imaging system 10 detects the radiation beam which penetrates the target patient to acquire the CBCT image.

Thereafter, the processor 110 acquires the final CBCT image for the target patient based on the plurality of CBCT images.

At this time, the processor 110 acquires a final CBCT image based on the plurality of CBCT images using one of the analytical reconstruction algorithm and the iterative reconstruction algorithm.

For example, referring to FIG. 11, the processor 110 reconstructs the plurality of CBCT images using the analytical reconstruction algorithm to acquire a final CBCT image for the target patient. That is, the processor 110 performs "a noise reduction process in a raw data domain"→"an image acquiring process by means of filtered back-projection (FBP) reconstruction method"→"a noise reduction process in an image domain" based on projection data (a plurality of CBCT images acquired by adaptive sampling according to the present disclosure) to acquire a final CBCT image. The part of reconstructing the image based on the analytical reconstruction algorithm is a known technique in the related art so that a detailed description will be omitted.

Further, referring to FIG. 12, the processor 110 reconstructs the plurality of CBCT images using the iterative reconstruction algorithm to acquire a final CBCT image for the target patient. That is, the processor 110 performs "the image acquiring process by the FBP reconstruction method", based on raw projection data (a plurality of CBCT images acquired by the adaptive sampling according to the present disclosure), and then, repeatedly performs "a process of acquiring projection data calculated by forward projection based on the image"→"a process of comparing raw projection data and calculated projection data"→"a process of updating an image according to a comparison result" to acquire a final CBCT image. The part of reconstructing the image based on the iterative reconstruction algorithm is a known technique in the related art so that a detailed description will be omitted.

The operation according to the exemplary embodiment of the present disclosure may be implemented as a program instruction which may be executed by various computers to be recorded in a computer readable storage medium. The computer readable storage medium indicates an arbitrary medium which participates to provide a command to a processor for execution. The computer readable storage medium may include solely a program command, a data file, and a data structure or a combination thereof. For example, the computer readable medium may include a magnetic medium, an optical recording medium, and a memory. The computer program may be distributed on a networked computer system so that the computer readable code may be stored and executed in a distributed manner. Functional programs, codes, and code segments for implementing the present embodiment may be easily inferred by programmers in the art to which this embodiment belongs.

The present embodiments are provided to explain the technical spirit of the present embodiment and the scope of the technical spirit of the present embodiment is not limited by these embodiments. The protection scope of the present embodiments should be interpreted based on the following appended claims and it should be appreciated that all technical spirits included within a range equivalent thereto are included in the protection scope of the present embodiments.

What is claimed is:

1. A CBCT image acquiring method based on adaptive sampling, comprising:
    a step of acquiring a plurality of image scanning points based on a previously acquired medical image for a target patient, by acquiring an image for every image scanning point based on the medical image, sorting images for image scanning points based on a quantitative value for each of images for image scanning points, selecting a plurality of images according to a predetermined criterion, among sorted images for image scanning points, and acquiring the image scanning points corresponding to the plurality of selected images as the plurality of image scanning points;
    a step of acquiring a plurality of cone beam computed tomography (CBCT) images for the target patient based on the plurality of image scanning points; and
    a step of acquiring a final CBCT image for the target patient based on the plurality of CBCT images.

2. The CBCT image acquiring method according to claim 1, wherein the step of acquiring a plurality of image scanning points is configured by sorting images for image scanning points based on an entropy for each of acquired images for image scanning points.

3. The CBCT image acquiring method according to claim 1, wherein the step of acquiring a plurality of image scanning points is configured by sorting the images for image scanning points in a descending order based on a quantitative value for each of the acquired images for image scanning points and selecting a plurality of images in the order of larger quantitative values, among the sorted images for image scanning points.

4. The CBCT image acquiring method according to claim 1, wherein the step of acquiring a plurality of image scanning points is configured by acquiring the image for every image scanning point from the medical image by means of forward projection, using geometric information of a CBCT imaging system.

5. The CBCT image acquiring method according to claim 1, wherein the step of acquiring a plurality of CBCT images is configured by scanning the target patient at the plurality of image scanning points by means of the CBCT scanning system to acquire the plurality of CBCT images.

6. The CBCT image acquiring method according to claim 1, wherein the step of acquiring a final CBCT image is configured by acquiring a final CBCT image based on the plurality of CBCT images using one of an analytical reconstruction algorithm and a iterative reconstruction algorithm.

7. The CBCT image acquiring method according to claim 1, wherein the medical image is a computed tomography volume image and the image scanning point is a gantry rotational index.

8. A computer program stored in a computer readable storage medium to allow a computer to execute the CBCT image acquiring method based on adaptive sampling according to claim 1.

9. A CBCT image acquiring apparatus which reconstructs a plurality of cone beam computed tomography images acquired based on adaptive sampling to acquire a final CBCT image, the apparatus comprising:
    a memory which stores one or more programs to acquire the final CBCT image by reconstructing the plurality of CBCT images acquired based on adaptive sampling; and
    a processor which performs an operation for reconstructing the plurality of CBCT images acquired based on adaptive sampling according to one or more programs stored in the memory to acquire the final CBCT image,
    wherein the processor acquires a plurality of image scanning points based on a previously acquired medical image for a target patient, acquires the plurality of CBCT images for the target patient based on the plurality of image scanning points, and acquires a final CBCT image for the target patient based on the plurality of CBCT images, and
    wherein the processor acquires an image for every image scanning point based on the medical image, sorts images for image scanning points based on a quantitative value for each of images for image scanning points, selects a plurality of images according to a predetermined criterion, among sorted images for image scanning points, and acquires the image scanning points corresponding to the plurality of selected images as the plurality of image scanning points.

10. The CBCT image acquiring apparatus according to claim 9, wherein the processor sorts images for image scanning points based on an entropy for each of acquired images for image scanning points.

11. The CBCT image acquiring apparatus according to claim 9, wherein the processor sorts the images for image scanning points in a descending order based on a quantitative value for each of the acquired images of every image scanning point and selects a plurality of images in the order of larger quantitative values, among the sorted images for image scanning points.

* * * * *